US00PP24159P2

(12) United States Plant Patent
Tas

(10) Patent No.: US PP24,159 P2
(45) Date of Patent: Jan. 14, 2014

(54) ***ALSTROEMERIA* PLANT NAMED 'TESSUNDAY IMPROVED'**

(50) Latin Name: *Alstroemeria hybrida*
Varietal Denomination: Tessunday Improved

(75) Inventor: Marius Tas, De Kwakel (NL)

(73) Assignee: VOF Hortipartners, Heerhugowaard (NL)

( * ) Notice: Subject to any disclaimer, the term of this patent is extended or adjusted under 35 U.S.C. 154(b) by 96 days.

(21) Appl. No.: 13/385,292

(22) Filed: Feb. 10, 2012

(51) Int. Cl.
*A01H 5/00* (2006.01)

(52) U.S. Cl.
USPC ..... Plt./309

(58) Field of Classification Search
USPC ..... Plt./309
See application file for complete search history.

*Primary Examiner* — Susan McCormick Ewoldt
(74) *Attorney, Agent, or Firm* — C. A. Whealy

(57) ABSTRACT

A new and distinct cultivar of *Alstroemeria* plant named 'Tessunday Improved', characterized by its upright and uniformly mounding plant habit; sturdy and strong plants; moderately vigorous growth habit; yellow and light red purple-colored flowers with short pedicels; and good garden performance.

1 Drawing Sheet

Botanical designation: *Alstroemeria hybrida.*
Cultivar denomination: 'TESSUNDAY IMPROVED'.

BACKGROUND OF THE INVENTION

The present invention relates to a new and distinct cultivar of *Alstroemeria* plant, botanically known as *Alstroemeria hybrida*, grown typically as a potted garden *Alstroemeria*, and hereinafter referred to by the name 'Tessunday Improved'.

The new *Alstroemeria* plant is a product of a planned breeding program conducted by the Inventor in Heerhugowaard, The Netherlands. The objective of the breeding program is to create new potted garden *Alstroemeria* plants that flower continuously and have attractive leaf and flower coloration.

The new *Alstroemeria* plant is a naturally-occurring branch mutation of *Alstroemeria hybrida* 'Tessunday', not patented. The new *Alstroemeria* plant was discovered and selected by the Inventor on a single flowering plant from within a population of plants of 'Tessunday' in a controlled greenhouse environment in Heerhugowaard, The Netherlands in June, 2008.

Asexual reproduction of the new *Alstroemeria* plant by root divisions in a controlled greenhouse environment in Heerhugowaard, The Netherlands since September, 2008 has shown that the unique features of this new *Alstroemeria* plant are stable and reproduced true to type in successive generations.

SUMMARY OF THE INVENTION

Plants of the new *Alstroemeria* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Tessunday Improved'. These characteristics in combination distinguish 'Tessunday Improved' as a new and distinct *Alstroemeria* plant:

1. Upright and uniformly mounding plant habit.
2. Sturdy and strong plants; moderately vigorous growth habit.
3. Yellow and light red purple-colored flowers with short pedicels.
4. Good garden performance.

Plants of the new *Alstroemeria* can be compared to plants of the mutation parent, 'Tessunday'. Plants of the new *Alstroemeria* differ from plants of 'Tessunday' in the following characteristics:

1. Plants of the new *Alstroemeria* are larger and more vigorous than plants of 'Tessunday'.
2. Plants of the new *Alstroemeria* have larger flowers than plants of 'Tessunday'.

Plants of the new *Alstroemeria* can be compared to plants of the *Alstroemeria hybrida* 'Tespurplin', not patented. In side-by-side comparisons, plants of the new *Alstroemeria* differ primarily from plants of 'Tespurplin' in flower color as plants of 'Tespurplin' have darker red purple-colored flowers with more and longer stripes. In addition, plants of the new *Alstroemeria* have larger flowers than plants of 'Tespurplin'.

BRIEF DESCRIPTION OF THE PHOTOGRAPH

The accompanying colored photograph illustrates the overall appearance of the new *Alstroemeria* plant showing the colors as true as it is reasonably possible to obtain in colored reproductions of this type. Colors in the photograph may differ slightly from the color values cited in the detailed botanical description which accurately describe the colors of the new *Alstroemeria* plant. The photograph comprises a side perspective view of a typical flowering plant of 'Tessunday Improved' grown in a container.

DETAILED BOTANICAL DESCRIPTION

The aforementioned photograph and following observations and measurements describe plants of the new *Alstro-*

*emeria* grown during the winter in 4.6-liter containers in a glass-covered greenhouse in Kudelstaart, The Netherlands. During the production of the plants, day temperatures ranged from 14° C. to 16° C. and night temperatures ranged from 12° C. to 14° C. Plants were 15 weeks old when the photograph and description were taken. Color references are made to The Royal Horticultural Society Colour Chart, 2007 Edition, except where general terms of ordinary dictionary significance are used.

Botanical classification: *Alstroemeria hybrida* 'Tessunday Improved'.

Parentage: Naturally-occurring branch mutation of *Alstroemeria hybrida* 'Tessunday', not patented.

Propagation:

*Type*.—By root divisions.

*Time to produce a rooted young plant, summer*.—About seven weeks at 20° C.

*Time to produce a rooted young plant, winter*.—About eight weeks at 16° C.

*Root description*.—Fibrous, fleshy; up to 2 cm in thickness; white in color.

*Rooting habit*.—Freely branching; medium density.

Plant description:

*Plant and growth habit*.—Upright and uniformly mounded habit; freely branching habit with about 23 primary lateral branches developing per plant, dense and bushy appearance; sturdy and strong plants; moderately vigorous growth habit.

*Plant height*.—About 23.5 cm.

*Plant diameter* (*area of spread*).—About 38.7 cm.

Lateral branch description:

*Aspect*.—Mostly upright to somewhat outwardly spreading.

*Length*.—About 12.3 cm.

*Diameter*.—About 5 mm.

*Internode length*.—About 9 mm.

*Strength*.—Moderately strong.

*Texture*.—Smooth, glabrous.

*Color*.—Close to N144D with a dull outer layer, close to 144D.

Foliage description:

*Arrangement*.—Alternate; below the peduncles in a single whorl; simple.

*Length*.—About 6.4 cm.

*Width*.—About 3 cm.

*Shape*.—Narrowly ovate to lanceolate.

*Apex*.—Acute.

*Base*.—Elongated and narrowly cuneate.

*Margin*.—Entire.

*Texture, upper and lower surfaces*.—Smooth, glabrous.

*Venation pattern*.—Parallel.

*Color*.—Developing leaves, upper surface: Close to 143B to 143C. Developing leaves, lower surface: Close to 143C. Fully expanded leaves, upper surface: Close to 137B and N138B; venation, close to 144A. Fully expanded leaves, lower surface: Close to N137B; venation, close to 143A to 143B.

*Petioles*.—Length: About 2.3 cm. Diameter: About 1 mm to 6 mm. Color: Close to 144A.

Flower description:

*Flower type and habit*.—Single zygomorphic flowers arranged in compound umbels; flowers face mostly outwardly; perianth segments separate; freely flowering habit with about seven flowers per inflorescence and about 150 flowers developing per plant.

*Natural flowering season*.—Plants begin flowering about eight weeks after planting; flowering continuous from early April through the summer in The Netherlands.

*Fragrance*.—None detected.

*Flower longevity on the plant*.—About ten days; flowers not persistent.

*Flower buds*.—Length: About 3.4 cm. Diameter: About 1.4 cm. Shape: Obovate. Color: Proximal half, close to 145D; distal, heavily tinged with close to 68B; venation, close to 143A to 143B.

*Umbel height*.—About 13.1 cm.

*Umbel diameter*.—About 15.2 cm.

*Flower diameter*.—About 8.4 cm by 8.1 cm.

*Flower depth* (*height*).—About 6 cm.

*Perianth*.—Arrangement: Six arranged in two whorls, each whorl with two lateral and one median segments. Size, inner perianth: Length, lateral segments: About 6.1 cm. Width, lateral segments: About 2.4 cm. Length, median segment: About 5.5 cm. Width, median segment: About 2.4 cm. Size, outer perianth: Length, all segments: About 6.2 cm. Width, all segments: About 3.9 cm. Shape, inner perianth, lateral and median segments: Narrowly obovate. Shape, outer perianth, lateral and median segments: Obcordate. Apex, inner perianth, lateral and median segments: Abruptly acute. Apex, outer perianth, lateral and median segments: Broadly retuse with a small abruptly acute point. Base, inner and outer perianths, lateral and median segments: Attenuate or cuneate. Margin, inner and outer perianths, lateral and median segments: Entire. Texture, inner and outer perianths, lateral and median segments: Smooth, glabrous. Color, inner perianth: When opening, all segments, upper surface: Close to 4B; towards the apex, close to N74C; apex, close to 146C to 146D; spots and streaks, close to 187A. When opening, all segments, lower surface: Close to 1D and 2C; towards the apex, close to N74D; central band, close to 63B; apex, close to 146C to 146D; spots and streaks, close to 195A. Fully opened, all segments, upper surface: Close to 12B; towards the apex, close to N74C; small central blotch, close to 63B; towards the base, close to 8C; spots and streaks, close to 187A; with development, color becomes closer to 77C with spots and streaks, close to 187B. Fully opened, all segments, lower surface: Close to 9C; towards the apex, close to N74D; central band, close to 63B; towards the base, close to 9D; spots and streaks, close to 195A. Color, outer perianth: When opening, all segments, upper surface: Towards the apex, close to 75A; apex, close to 146B; towards the base, close to 4D; central blotch, close to 70B. When opening, all segments, lower surface: Towards the apex, close to 75B; apex, close to 146B; towards the base, close to 157C; central blotch, close to 70B. Fully opened, all segments, upper surface: Towards the apex, close to 75A to 75C and N74C; apex, close to 146B to 146C; towards the base, close to 155C; central blotch, close to 70B. Fully opened, all segments, lower surface: Towards the apex, close to 75A to 75B; apex, close to 146B; towards the base, close to 155C; central blotch, close to 64B.

*Pedicels*.—Length: About 1.8 cm. Diameter: About 2 mm. Strength: Moderately strong. Angle: Erect to about 30° from vertical. Texture: Smooth, glabrous. Color: Close to 143B.

*Reproductive organs*.—Stamens: Quantity per flower: Six. Filament length: About 3.7 cm. Filament color: Close to 75A; towards the base, close to 75D. Anther shape: Oblong to elliptical. Anther length: About 7 mm. Anther color: Close to 152D. Pollen amount: Moderate. Pollen color: Close to 195B to 195C. Pistils: Quantity per flower: One. Pistil length: About 3.9 cm. Style length: About 3.4 cm. Style color: Close to 76B to 76D. Stigma shape: Tri-parted; parts, club-shaped, curved. Stigma color: Close to 70A to 70B. Ovary color: Close to 144A.

*Fruits and seeds*.—Fruit and seed development have not been observed on plants of the new *Alstroemeria*.

Disease & pest resistance: Plants of the new *Alstroemeria* have not been observed to be resistant to pathogens and pests common to *Alstroemeria* plants.

Garden performance: Plants of the new *Alstroemeria* have been observed to have good garden performance and to tolerate wind and rain. Plants of the new *Alstroemeria* have been observed to tolerate high temperatures of about 35° C. and to be hardy to USDA Hardiness Zone 8.

It is claimed:

1. A new and distinct *Alstroemeria* plant named 'Tessunday Improved' as illustrated and described.

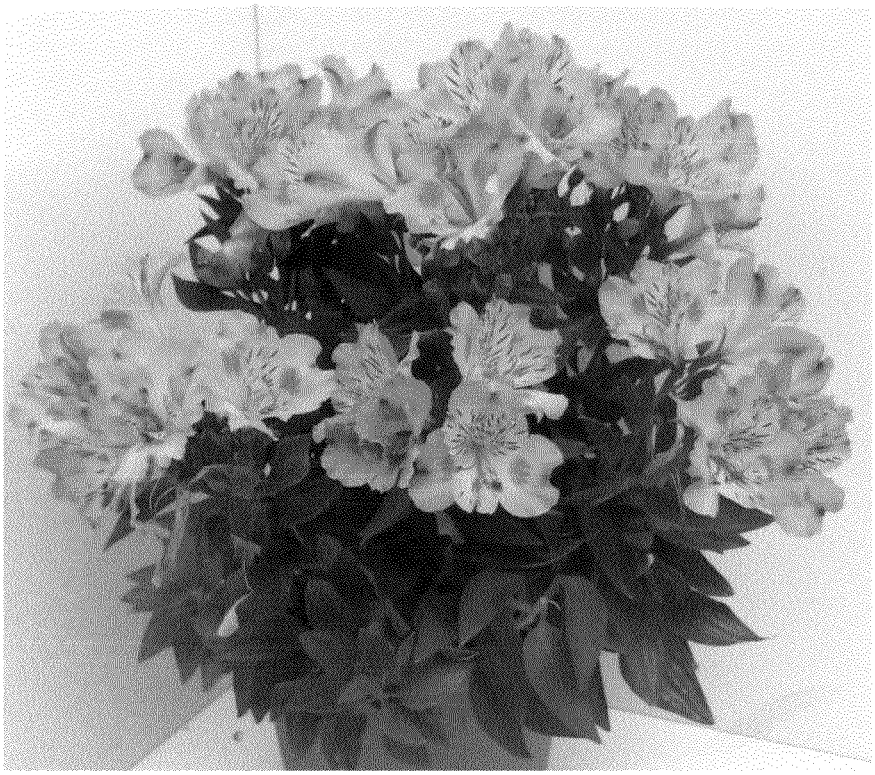

* * * * *